United States Patent [19]

Hertel et al.

[11] Patent Number: 4,565,894
[45] Date of Patent: Jan. 21, 1986

[54] PREPARATION OF IONONES

[75] Inventors: Otto Hertel, Ludwigshafen; Hans Kiefer, Wachenheim; Lothar Arnold, Heidelberg, all of Fed. Rep. of Germany

[73] Assignee: BASF Aktiengesellschaft, Ludwigshafen, Fed. Rep. of Germany

[21] Appl. No.: 637,890

[22] Filed: Aug. 6, 1984

[30] Foreign Application Priority Data

Aug. 6, 1983 [DE] Fed. Rep. of Germany ....... 3328440

[51] Int. Cl.$^4$ .............................................. C07C 49/21
[52] U.S. Cl. .................................... 568/349; 568/343
[58] Field of Search ................................ 568/343, 349

[56] References Cited

U.S. PATENT DOCUMENTS

| | | | |
|---|---|---|---|
| 2,877,271 | 3/1959 | Kaiser et al. | 568/343 |
| 3,475,764 | 10/1969 | Pot et al. | 568/349 |
| 3,480,677 | 7/1957 | Mevly | 568/349 |
| 3,886,215 | 5/1975 | Desimone | 568/349 |

FOREIGN PATENT DOCUMENTS

| | | | |
|---|---|---|---|
| OZ24211 | 4/1966 | Fed. Rep. of Germany | 568/349 |
| 1283835 | 11/1968 | Fed. Rep. of Germany | 568/349 |
| 2029561 | 12/1971 | Fed. Rep. of Germany | 568/349 |
| 1410645 | 10/1965 | France | 568/349 |
| 1156443 | 1/1968 | United Kingdom | 568/349 |
| 1191089 | 4/1969 | United Kingdom | 568/349 |
| 458540 | 11/1962 | U.S.S.R. | 568/349 |
| 547445 | 7/1975 | U.S.S.R. | 568/349 |

OTHER PUBLICATIONS

Noller, "Chemistry of Carbon Compounds", (1965) p. 955.
Abstract of "β-Ionone" by Tomuljak, D. et al., Czech 179,046, Jun. 15, 1979, Appl. 74/3,229, May 6, 1974; 2 pp., 92:146997b.

*Primary Examiner*—Werren B. Lone
*Attorney, Agent, or Firm*—Oblon, Fisher, Spivak, McClelland & Maier

[57] ABSTRACT

Ionones are prepared by cyclization of pseudoionone with concentrated sulfuric acid in the presence of an organic solvent or diluent, while cooling, and by dilution of the reaction mixture with water, by a continuous process in which the pseudoionone is combined with an aliphatic or cycloaliphatic hydrocarbon which boils at 25°–65° C. under the reaction conditions, or an aliphatic chlorohydrocarbon, and the sulfuric acid, with thorough mixing and evaporative cooling by partial or complete vaporization of the solvent present in the reaction mixture, combination being effected so that the temperature of the reaction mixture is from 25° to 65° C. and the residence time of this mixture before it is diluted with water is from 0.5 to 20, preferably from 0.1 to 5, seconds.

The novel process can be used to prepare α- and β-ionone in a technically simple and advantageous manner and in very good yields.

10 Claims, No Drawings

PREPARATION OF IONONES

The present invention relates to an improved process for the continuous preparation of α- and/or β-ionone by cyclization of pseudoionone by means of concentrated sulfuric acid in the presence of an organic solvent or diluent and by diluting the reaction mixture with water.

It is known that the cyclization of pseudoionone in the presence of an acid, such as sulfuric acid or phosphoric acid, gives a mixture of α- and β-ionone. The ratio in which these compounds are formed depends to a great extent on the conditions under which the reaction takes place.

Since both α-ionone and β-ionone are very important industrially, there has been no lack of attempts to provide a very advantageous process for their preparation.

Processes for the cyclization of pseudoionone with concentrated sulfuric acid have proven particularly useful. Since this reaction is highly exothermic, it is very important that the resulting heat of reaction is conducted away very rapidly, in order to avoid localized overheating. To do this, diluents have been added to the reaction mixture in the conventional processes. For example, according to German Pat. Nos. 1,080,105 and 1,668,505, aliphatic or cycloaliphatic hydrocarbons are used. A disadvantage of this process is that resins are deposited relatively rapidly in the reaction vessels and interfere with the continuous operation.

According to Indian Pat. No. 77,225, the reaction is carried out in the presence of an aliphatic chlorohydrocarbon, such as methylene chloride, ethylene dichloride, chloroform or carbon tetrachloride, at from $-10°$ C. to $+10°$ C.

According to the description in German Laid-Open Application DOS 1,568,108, this Indian process is disadvantageous because the aliphatic chlorohydrocarbons react with sulfuric acid to eliminate hydrogen chloride, with the result that the apparatuses used are corroded in a short time. To avoid these disadvantages, it is recommended that the cyclization be carried out at from $-25$ to $10°$ C. in a mixture of low boiling hydrocarbons and chlorohydrocarbons. The disadvantage of the two last-mentioned processes is that the reaction temperature has to be kept low in order to achieve good yields of ionone, expensive coolants being required for this purpose.

In other conventional processes, the substantial heat of cyclization is conducted away by evaporative cooling with liquefied gases. For example, the process of German Pat. No. 1,668,496 uses liquid sulfur dioxide, that of German Pat. No. 1,668,505 employs propane, butane or isobutane, and that of German Pat. No. 1,917,132 uses methyl chloride and is carried out at from $-25°$ C. to room temperature, preferably at below $+10°$ C.

The results obtained using these processes are in general very good. Their disadvantage is the great expense entailed in reliquefying the gas vaporized in the reaction.

Furthermore, Czechoslovakian Pat. No. 179,046 and U.S.S.R. Pat. Nos. 458,540 and 547,445 disclose processes for the preparation of β-ionone, in which thorough mixing of the reactants and rapid removal of heat are achieved by using a thin-film reactor. The disadvantage of the two last-mentioned processes is that only about 3–6 kg of β-ionone per $m^2$ of thin film per hour are obtained, and hence extrapolation to the industrial scale would require extremely large apparatuses. A disadvantage of the process of the Czechoslovakian patent is that, in order to obtain good yields, the procedure has to be carried out at from $10°$ to $15°$ C., so that expensive coolants are once again required.

All of the conventional processes always give a mixture of α- and β-ionone. According to German Pat. Nos. 1,080,105, 1,668,496 and 1,668,505, β-ionone is preferentially obtained at reaction temperatures of from $-20°$ to $0°$ C., while the α-ionone content increases at from $-10°$ to $25°$ C. β-Ionone is an important intermediate for the industrial production of vitamin A, and a high content of α-ionone leads to a reduced yield in this preparation. On the other hand, pure α-ionone is a desirable scent, which would be adversely affected by a fairly high content of β-ionone.

It is an object of the present invention to provide a process which permits the preparation of both very pure α-ionone and very pure β-ionone in a very advantageous manner and in high yields and space-time yields.

We have found that this object is achieved by a very advantageous process for the continuous preparation of ionones by cyclization of pseudoivance with concentrated sulfuric acid in the presence of an organic solvent or diluent, while cooling, and by dilution of the reaction mixture with water, wherein the pseudoionone is combined with an aliphatic or cycloaliphatic hydrocarbon which boils at $25°–65°$ C. under the reaction conditions, or an aliphatic chlorohydrocarbon, and the sulfuric acid, with thorough mixing and evaporative cooling by partial or complete vaporization of the solvent present in the reaction mixture, combination being effected so that the temperature of the reaction mixture is from $25°$ to $65°$ C., preferably from $30°$ to $55°$ C., in particular from $35°$ to $45°$ C., and the residence time of this mixture before it is diluted with water or dilute sulfuric acid is from 0.05 to 20, preferably from 0.1 to 5, seconds.

In a particularly advantageous embodiment of the novel process, the pseudoionone is combined with a solvent which boils at from $25°$ to $65°$ C. under atmospheric pressure, preferably methylene chloride or chloroform, in particular methylene chloride, and with the sulfuric acid, with thorough mixing and evaporative cooling by partial vaporization of the solvent present in the reaction mixture.

The novel process displays a further advantage if dilution of the reaction mixture with water is also carried out with evaporative cooling by vaporization of the solvent present in the reaction mixture.

We have furthermore found that the ratio of α-ionone to β-ionone in the reaction product is very greatly influenced by the amount of sulfuric acid used.

In the novel process, α-ionone is predominantly obtained if about 2–3 moles of concentrated sulfuric acid are used per mole of pseudoionone, and β-ionone is predominantly obtained if more than 5, i.e. about 5–15, moles of sulfuric acid are employed per mole of pseudoionone.

The results obtained are surprising since it is emphasized in virtually all of the conventional methods that good yields of ionones, in particular of β-ionone, are obtained in the cyclization of pseudoionone with sulfuric acid only when the process is carried out at very low temperatures.

The reaction according to the invention gives space-time yields which are so good that very small reaction vessels can be employed; it is therefore possible to use glass apparatuses, so that corrosion problems, which may occur when aliphatic halohydrocarbons are used as solvents, are avoided.

The novel cyclization reaction can be carried out in principle in a suitable thin-film reactor, a simple nozzle, a static mixer or any mixing zone.

The cyclization can be particularly advantageously carried out in a short mixing zone.

Recovery of the vaporized solvent by distillation can be carried out in a relatively simple manner, since it is sufficient to use river water as a coolant for the condensation.

The concentration of the sulfuric acid used in the cyclization can be from 90 to 100% by weight, and 95-98% strength commercial sulfuric acid is preferably used. In general, from 2 to 15, preferably from 2 to 7, moles of sulfuric acid are used per mole of pseudoionone. The use of from 2 to 3 moles of sulfuric acid per mole of pseudoionone gives predominantly α-ionone, whereas the use of more than 5 moles of sulfuric acid per mole of pseudoionone results in β-ionone containing less than 2% of α-ionone.

Suitable solvents are essentially aliphatic or cycloaliphatic hydrocarbons or aliphatic chlorohydrocarbons which boil at from 25° to 65° C. under the reaction conditions. Examples are pentane, hexane, isopentane, cyclohexane, methylene chloride, chloroform, carbon tetrachloride, 1,2-dichloroethane and 1,1,1-trichloroethane. In the case of solvents which boil at above 65° C. under atmospheric pressure, the optimum reaction temperatures tures of about 35°-45° C. are established by reducing the pressure in the reaction vessel. It is of course particularly advantageous to use solvents which boil at from 25° to 65° C. under atmospheric pressure. Chloroform (bp.=61.3° C.) or, in particular, methylene chloride (bp.=41.6° C.) is preferably used.

The amount of solvent can be varied within wide limits, but the best results are obtained if about 1-5, preferably 1.5-3, parts by volume of solvent are used per part by volume of pseudoionone.

The amount of solvent used depends on whether the heat of reaction produced when the reaction mixture is diluted with water is to be conducted away by evaporative cooling, this being a particularly advantageous procedure.

When the reaction is complete, the reaction mixture is immediately diluted with water, as a rule from 0.8 to 2 l of water per kg of sulfuric acid being used. In this context, it is advisable to ensure that the heat of hydration of the sulfuric acid does not result in the temperature exceeding 50° C. This can be achieved by conducting away the heat, likewise by evaporative cooling with appropriate amounts of solvent.

The higher the concentration of the dilute sulfuric acid obtained as a by-product in the process, the more easily can this acid be utilized. It is therefore technically and economically advantageous if the reaction mixture consisting of the solvent, the ionones and the concentrated sulfuric acid is diluted not with pure water but with dilute, about 20-50% strength by weight, sulfuric acid; it is of course possible to use the dilute acid formed in the process after this acid has been cooled. If the concentration of this acid before dilution of the reaction mixture is, for example, 45% by weight, the freshly fed in concentrated sulfuric acid gives, after the dilution step, a more highly concentrated acid, e.g. a 60% strength by weight acid. In steady-state operation, some of this acid is removed from the system while the remaining part is cooled, brought to 45% by weight once again with fresh water, and recycled.

The process according to the invention can be used to prepare α- and β-ionone in a technically simple and advantageous manner and in very good yields.

EXAMPLE 1

(a) Description of the apparatus

The mixing chamber consisted of a vertical glass tube which was filled with Raschig rings and had an internal diameter of 2 cm and a height of 30 cm, the separate feed pipes for the pseudoionone solution and the concentrated sulfuric acid being located at the upper end of this tube.

A 5 cm high connecting piece was located below the tube, and was provided with a nozzle for spraying in the diluting water or the dilute sulfuric acid.

The connecting piece was in turn mounted on a condenser, which was used for condensing the solvent. Below the condenser was a separator, which was provided with the appropriate take-off pipes and used for phase separation.

(b) Carrying out the reaction

A solution of 600 g of pseudoionone in 1,200 ml of methylene chloride, and 1,130 ml of concentrated sulfuric acid (96% strength), were fed simultaneously into the apparatus described above, in the course of 4 minutes, via two glass tubes. The major part of the heat of reaction produced when the two solutions met was conducted away by vaporization of methylene chloride, so that the reaction mixture was at about 41° C. The methylene chloride vapor formed forced the reaction mixture very rapidly through the mixing chamber, so that the residence time was only about 0.5 second.

The reaction mixture leaving the mixing chamber, at about 41° C., was immediately mixed with a total of 2,000 ml (500 ml/minute) of water introduced through the nozzle, after which the mixture passed through the condenser and into the separator. Here, the methylene chloride phase was separated from the aqueous sulfuric acid phase. The aqueous phase was extracted with twice 400 ml of methylene chloride, the combined extracts were brought to pH 8-9 with 15% strength sodium carbonate solution, the solvent was separated off by distillation, and the residue was distilled under 0.1 mbar. The yield was 82.7% of β-ionone and 2.7% of α-ionone. The residue consisted of a resin which exhibited good flow and could be incinerated without causing pollution.

EXAMPLES 2 TO 8

A solution of, in each case, 600 g of pseudoionone in the solvent stated in the Table (which also shows the amount of solvent used), and the amount of concentrated sulfuric acid also shown in the Table, were introduced simultaneously into the apparatus described in Example 1a, in the times shown in the Table, the procedure being similar to that described in Example 1b. The temperature in the mixer and the mean residence time are stated in the Table. The total amount of water shown in the Table was immediately added, via the nozzle, to the reaction mixture leaving the mixing chamber, after which the mixture passed via the condenser into the separator. The reaction mixture was worked up by a procedure similar to that described in Example 1b, and the resulting yields of α- and β-ionone are stated in the Table.

In Example 8, the reaction mixture leaving the mixing chamber was mixed with 40% strength by weight sulfuric acid instead of water.

TABLE 1

| Example | Solvent | Amount [ml] | Concentrated $H_2SO_4$ [ml] | Duration of experiment [min.] | Temperature in the mixer [°C.] | Mean residence time [seconds] | Water [ml] | Yield β-ionone | Yield α-ionone |
|---|---|---|---|---|---|---|---|---|---|
| 2 | $CH_2Cl_2$ | 1200 | 1150 | 2 | 41 | 0.5 | 2000 | 85% | 3% |
| 3 | $CH_2Cl_2$ | 1100 | 1050 | 1.5 | 41 | 0.4 | 2300 | 89.7% | 1.7% |
| 4 | $CH_2Cl_2$ | 900 | 380 | 1.5 | 41 | 1.0 | 2000 | 33% | 51% |
| 5 | $CH_2Cl_2$ | 900 | 1070 | 6 | 41 | 1.5 | 3000 | 87.4% | 1.2% |
| 6 | $CHCl_3$ | 1200 | 1180 | 1.5 | 61 | 0.5 | 2000 | 84.6% | 2.5% |
| 7* | Hexane | 1400 | 1100 | 1.5 | 45 | 0.5 | 2000 | 81% | 2.0% |
| 8** | $CH_2Cl_2$ | 1200 | 1130 | 1.5 | 51 | 0.5 | 2000** | 88.9% | 2.0% |

*Experiment 7 was carried out under 1,300 mbar.
**In Experiment 8, the reaction mixture was diluted with 40% strength by weight sulfuric acid.

EXAMPLE 9

(a) Description of the apparatus

The reaction vessel used was a thin film evaporator which consisted of a vertical glass tube which was open at the bottom, had a length of 40 cm and a diameter of 2.2 cm and was provided with a metal stirrer possessing 4 movable pairs of blades. The 4 pairs of blades were 20 cm long and swept through an area of 0.014 m². The two reactants were introduced into the upper reaction space through two separate connections. The solvent vaporized during the reaction was condensed, and was recycled to the reactor. The discharged reaction mixture was decomposed with water in a second thin film reactor. Here too, the vaporized solvent was condensed and recycled.

(b) Carrying out the reaction

A solution of 600 g of a 96% pure pseudoionone in 1,200 ml of methylene chloride was introduced continuously in the course of 10 minutes, while stirring vigorously (800 rpm), through one of the two connections of the reactor, and 1,000 ml of a 96% strength sulfuric acid were fed in simultaneously through the other connection. The product, which was discharged at 42° C., was hydrolyzed in a downstream thin film reactor with 2,000 ml of water, the organic phase was separated off, washed neutral with 2% strength sodium carbonate solution and then with water and freed from solvent under reduced pressure, and the residue was then distilled under 0.2 mbar. 495 g of 97.0% pure β-ionone were obtained, corresponding to a yield of β-ionone of 83.3% of theory. In this case too, the residue produced was a resin which exhibited good flow.

EXAMPLE 10

The procedure was carried out exactly as described in Example 9, except that the solution of 600 g of a 96% pure pseudoionone in 1,200 ml of methylene chloride, and the 1,000 ml of sulfuric acid, were introduced simultaneously into the reactor in the course of 5 minutes instead of 10 minutes. The distillation gave 490 g of a 98% pure β-ionone, corresponding to a yield of β-ionone of 83.4% of theory.

EXAMPLES 11 to 18

Examples 11 to 18 were carried out similarly to Example 9. The specific reaction parameters and the yields are summarized in the Table below.

TABLE 2

| Example | Solvent | Amount [ml] | Concentrated $H_2SO_4$ [ml] | Pressure [mbar] | Duration of experiment [min] | Temperature in the mixer [°C.] | Mean residence time [seconds] | Water [ml] | Yield β-ionone | Yield α-ionone |
|---|---|---|---|---|---|---|---|---|---|---|
| 11 | $CHCl_3$ | 1200 | 1100 | 280 | 11.5 | 35 | 2 | 2000 | 85 | 2.0 |
| 12 | $CCl_4$ | 1200 | 1040 | 210 | 11 | 40 | 2 | 2000 | 78 | 2.5 |
| 13 | $ClCH_2-CH_2-Cl$ | 1200 | 900 | 210 | 10 | 45 | 2 | 2000 | 83 | 2.4 |
| 14 | $CH_3-CCl_3$ | 1200 | 1070 | 250 | 12 | 42 | 2 | 2000 | 82 | 2.0 |
| 15 | Hexane | 1200 | 1070 | 250 | 11 | 35 | 2 | 2000 | 80 | 2.7 |
| 16 | Cyclohexane | 1200 | 1120 | 250 | 11 | 45 | 2 | 2000 | 76 | 1.8 |
| 17 | Pentane | 1200 | 1015 | 1013 | 9.5 | 40 | 2 | 3000 | 76 | 2.5 |
| 18* | $CHCl_3$ | 1200 | 1080 | 1013 | 10 | 48 | 2 | 2000 | 83 | 2.1 |

*In this experiment, the thin-film reactor was cooled with water.

We claim:

1. A process for the continuous preparation of ionones by cyclization of pseudoionone with concentrated sulfuric acid in the presence of an organic solvent or diluent, while cooling, and by dilution of the reaction mixture with water, wherein the pseudoionone is combined with an aliphatic or cycloaliphatic hydrocarbon which boils at 25°–65° C. under the reaction conditions, or an aliphatic chlorohydrocarbon, and the sulfuric acid, with thorough mixing and evaporative cooling by partial or complete vaporization of the solvent present in the reaction mixture, combination being effected so that the temperature of the reaction mixture is from 25° to 65° C. and the residence time of this mixture before it is diluted with water is from 0.05 to 20 seconds.

2. A process as claimed in claim 1, wherein the pseudoionone is combined with a solvent which boils at 25°–65° C. under atmospheric pressure and with the sulfuric acid, with thorough mixing and evaporative cooling by partial or complete vaporization of the solvent present in the reaction mixture.

3. A process as claimed in claim 1, wherein the pseudoionone is combined with methylene chloride as a solvent and with sulfuric acid, with thorough mixing and evaporative cooling by partial or complete vaporization of the methylene chloride present in the reaction mixture.

4. A process as claimed in claim 1, wherein the pseudoionone is combined with the solvent and the sulfuric acid with thorough mixing and evaporative cooling, combination being effected so that the temperature of the reaction mixture is from 30° to 55° C.

5. A process as claimed in claim 1, wherein dilution of the reaction mixture with water is also carried out with evaporative cooling by vaporization of the solvent present in the reaction mixture.

6. A process as claimed in claim 1, wherein in order to prepare predominantly α-ionone, the pseudoionone is combined with the solvent and only from 2 to 3 moles of sulfuric acid per mole of pseudoionone, with thorough mixing and evaporative cooling.

7. A process as claimed in claim 1, wherein, in order to prepare predominantly β2-ionone, the pseudoionone is combined with the solvent and more than 5 moles of sulfuric acid per mole of pseudoionone, with thorough mixing and evaporative cooling.

8. A process as claimed in claim 1, wherein the water used for diluting the reaction mixture contains about 20–50% by weight of sulfuric acid.

9. The process of claim 1, wherein said residence time is from 0.1 to 5 seconds.

10. The process of claim 4, wherein the temperature of the reaction mixture is from 35° to 45° C.

* * * * *